United States Patent [19]

Kraff

[11] Patent Number: 4,990,159
[45] Date of Patent: Feb. 5, 1991

[54] INTRAOCULAR LENS APPARATUS WITH HAPTICS OF VARYING CROSS-SECTIONAL AREAS

[76] Inventor: Manus C. Kraff, 5600 W. Addison, Chicago, Ill. 60634

[21] Appl. No.: 279,572

[22] Filed: Dec. 2, 1988

[51] Int. Cl.⁵ .............................................. A61F 2/16
[52] U.S. Cl. .................................................... 623/6
[58] Field of Search ........................................ 623/6

[56] References Cited

U.S. PATENT DOCUMENTS

| | | | |
|---|---|---|---|
| Re. 31,963 | 8/1985 | Kelman | 623/6 |
| 4,092,743 | 6/1978 | Kelman | 623/6 |
| 4,134,160 | 1/1979 | Bayers | 623/6 |
| 4,159,546 | 7/1979 | Shearing | 623/6 |
| 4,268,921 | 5/1981 | Kelman | 623/6 |
| 4,296,501 | 10/1981 | Kelman | 623/6 |
| 4,338,687 | 7/1982 | Rainin | 623/6 |
| 4,343,050 | 8/1982 | Kelman | 623/6 |
| 4,403,354 | 9/1983 | Rainin | 623/6 |
| 4,494,254 | 1/1985 | Lopez | 623/6 |
| 4,527,294 | 7/1985 | Heslin | 623/6 |
| 4,536,896 | 8/1985 | Bittner | 623/6 |
| 4,576,607 | 3/1986 | Kelman | 623/6 |
| 4,578,078 | 3/1986 | Arkell et al. | 623/6 |
| 4,581,032 | 4/1986 | Grandon | 623/6 |
| 4,585,454 | 4/1986 | Fabricant | 623/6 |
| 4,586,930 | 5/1986 | Kelman | 623/6 |
| 4,588,405 | 5/1986 | Knolle, Jr. | 623/6 |
| 4,591,358 | 5/1986 | Kelman | 623/6 |
| 4,600,003 | 7/1986 | Lopez | 128/303 |
| 4,600,004 | 7/1986 | Lopez et al. | 128/303 |
| 4,601,720 | 7/1986 | Sinsky | 623/6 |
| 4,601,721 | 7/1986 | Kamerling | 623/6 |
| 4,601,722 | 7/1986 | Kelman | 623/6 |
| 4,615,701 | 10/1986 | Woods | 623/6 |
| 4,617,023 | 10/1986 | Peyman | 623/6 |
| 4,619,256 | 10/1986 | Horn | 128/303 |
| 4,619,656 | 10/1986 | Lindstrom | 623/6 |
| 4,629,461 | 12/1986 | Clayman et al. | 623/6 |
| 4,636,210 | 1/1987 | Hoffer | 623/6 |
| 4,642,113 | 2/1987 | Dubroff | 623/6 |
| 4,681,585 | 7/1987 | Sayano et al. | 623/6 |
| 4,701,181 | 10/1987 | Arnott | 623/6 |
| 4,704,123 | 11/1987 | Smith | 623/6 |
| 4,710,195 | 12/1987 | Giovinazzo | 623/6 |
| 4,726,367 | 2/1988 | Shoemaker | 623/6 UX |
| 4,738,680 | 4/1988 | Herman | 623/6 |

Primary Examiner—Ronald L. Frinks
Attorney, Agent, or Firm—Dick and Harris

[57] ABSTRACT

An intraocular lens apparatus for replacement of the natural lens following the extraction of the natural lens in cataract surgery. One or more resilient haptics, having one or both ends affixed to the lens body, are provided with alternating regions of varying transverse cross-sectional area along their length, so as to combine a relatively narrow insertion profile with great flexibility and stability once implanted within the eye.

16 Claims, 3 Drawing Sheets

INTRAOCULAR LENS APPARATUS WITH HAPTICS OF VARYING CROSS-SECTIONAL AREAS

BACKGROUND OF THE INVENTION

In cataract surgery, the clouded natural lens is normally removed. An artificial lens known as an intraocular lens, or IOL, is implanted within either the posterior chamber or the anterior chamber of the eye. The IOL comprises an optic lens portion and a portion to retain and support the lens within the eye. The supporting and retaining portion usually employs one or more elongated strands, referred to as loops or haptics, which are resiliently deformable to facilitate insertion of the IOL into the eye, and expansion of the portion bearing against the interior surface of the eye, once implanted. The present invention relates in general to such an intraocular lens apparatus, and in particular, to a posterior chamber intraocular lens apparatus having loop-shaped haptics having areas of varying transverse cross-sectional area, so as to minimize the effective maximum width dimension or transverse profile of the IOL upon insertion through the smallest possible incision, and maximize the region of contact by the haptics with the interior surface of the eye upon implantation for greater stability.

In order to effectively utilize an intraocular lens within the eye, the clouded natural lens must first be removed prior to insertion of the IOL. Such removal can be achieved by a number of different processes. One such process is phacoemulsification, wherein a microneedle is vibrated approximately forty thousand times per second so as to effectively liquify the nucleus of the natural lens for facilitated removal. Once this occurs, the remainder of the natural lens is removed from the eye by a finely regulated suction process.

In cataract surgery, it is extremely important to keep the incision made in the eye, which provides access to the posterior chamber, as small as possible in order to speed the healing process. While several prior art IOLs have employed haptics configured so as to provide the narrowest transverse profile and thereby enable insertion of the IOL through the smallest possible incision in the eye, few, if any such IOLs, have been designed so as to allow for a maximum region of contact with the interior surface of the eye after implantation and positioning within the eye. Likewise, such narrow profile prior art IOL's tend to have relatively rigid haptics that tend to increase the risk of puncturing or scratching the interior of the eye. Furthermore, no known prior art IOL incorporates a haptic which is configured so as to have alternating regions of varying transverse cross-sectional areas along the length of the haptic which serve to combine a narrow insertion profile with great flexibility for maximum stability upon implantation within the eye.

Historically, conventional IOLs have been of either the C-loop type or the J-loop type.

J-loop haptics have a thin insertion profile and relatively stiff legs extending outwardly in a nearly straight, tangential fashion from the lens, and have a small, sharply curved open end. Hence, J-loop haptics provide a higher potential for damaging (by scratching or puncturing) the interior of the eye, and at times are less stable, once implanted, due to their increased, almost column-like rigidity.

C-loop haptics provide improved stability upon insertion, in light of their prolonged, smoother curved regions of contact with the interior of the eye, but require larger incisions and usually more manipulation upon insertion, as a result of their wide profile. Examples of prior art J-loop haptics are U.S. Pat. Nos. 4,159,546; 4,581,031; and 4,636,210, while examples of prior art C-loop haptics are U.S. Pat. Nos. 4,535,896; 4,585,456; 4,601,722; and 4,629,461.

It is thus an object of the present invention to provide a posterior chamber intraocular lens apparatus which can be inserted through a relatively small axial incision in the eye, that is smaller than the incision required for a normal C-type haptic, much like a J-type haptic, while retaining the retention and increasing stability capabilities of a C-type haptic, once implanted.

It is another object of the present invention to provide a posterior chamber intraocular lens apparatus which employs regions of varying cross-sectional area along the length of its haptics to maximize flexibility and, in turn, the region of contact with the interior of the eye once inserted.

Another object of the present invention is to provide a posterior chamber intraocular lens apparatus which can be easily manipulated into proper position once it has been inserted into the eye, while also reducing the risk of damaging the interior of the eye during such manipulation.

It is another object of the invention to provide a new and improved posterior chamber intraocular lens that assumes the shape of the intraocular confines, such as the capsular bag or ciliary sulcus, because of the increased flexibility of the haptic design.

It is another object of the invention to provide a new and improved posterior chamber intraocular lens apparatus which avoids one or more of the above-mentioned limitations and disadvantages of prior art intraocular lenses.

These and other objects of the present invention, shall become apparent from the description of the drawings and claims that follow.

SUMMARY OF THE INVENTION

The present invention relates to an intraocular lens apparatus for implantation in the posterior chamber of an eye, in which the apparatus is to be inserted into the eye along a longitudinal or radial direction with respect to the center of the eye through a relatively small incision which is made in the eye along the outer periphery of the corneal-scleral junction. The apparatus is configured in such a way as to have strong, yet flexible support means which are used for positioning, and maintaining the position, of the apparatus once it has been inserted within the interior of the eye, and to further enable ease of manipulation, rotation and positioning of the apparatus after it has been inserted into the posterior chamber of the eye.

The intraocular lens apparatus includes a substantially circular transparent optical, light-focusing lens means which includes an anterior side, and an opposite posterior side, as well as a peripheral edge. The apparatus may or may not also include positioning means which are operably attached to the lens means, and which serve to enable facilitated manipulation of the intraocular lens apparatus once it has been inserted within the eye, thereby enabling proper positioning therewithin. Resilient support means are also a structural feature of the intraocular lens apparatus. These resilient support means are operably attached to the lens means, and they extend outwardly therefrom, and serve to retain and stabilize the intraocular lens apparatus once it has been appropriately located within the eye by contacting the eye interior along a region of contact. The resilient support means additionally comprises at least one flexible loop member which has a plurality of regions of increased cross-section which are each positioned next to a region of narrowed cross-section, along its length, so as to maximize the length of the region of contact within the interior of the eye.

In the preferred embodiment of the invention, the support means further comprises loop members which are operably attached at a first end to the peripheral edge of the lens means and end at a second end. These regions of narrowed cross-section of the loop member have successively smaller transverse cross-sectional areas than the next preceding region of the narrowed cross-section. Furthermore, each of the regions of narrowed cross-sections decrease in transverse cross-sectional area from the next preceding narrowed region along the length of the loop member from the first end to the second end, so as to provide for greater flexibility of the loop member proximate to its second end.

In another embodiment of the invention, the support means further comprises loop members which are operably attached at a first end to the peripheral edge of the lens means, and which end at a second end. Each of the regions of narrowed cross-section of the loop member has a successively smaller, constant transverse cross-sectional area than the next preceding region of narrowed cross-section as one moves from the first end to the second end. Furthermore, each of the regions of narrowed cross-section progressively increase in transverse cross-sectional area along the length of the loop member from the next preceding narrowed region, from the first end to the second end, so as to provide for greater flexibility of the loop member proximate to its first end.

In yet another embodiment of the invention, the support means further comprises loop members which are operably attached at a first end to the peripheral edge of the lens means, and which end at a second end. Each of the regions of increased cross-section of the loop member has successively smaller transverse cross-sectional areas than the next preceding region of increased cross-section. In addition, each of the regions of increased cross-section increase in transverse cross-sectional area from the next preceding narrowed region along the length of the loop member, from the first end to the second end, so as to provide for greater flexibility of the loop member proximate to its first end.

The support means in another embodiment of the invention, further comprises loop members being operably attached at a first end to the peripheral edge of the lens means and ending at a second end. The regions of increased cross-section of the loop member have successively smaller transverse cross-sectional areas than the next preceding region of the increased cross-section, as one moves from the first end to the second end. In addition, each of the regions of the increased cross-section decrease in transverse cross-sectional area from the one preceding it along the length of the loop member, from the first end to the second end, so as to provide for greater flexibility of the loop member proximate to its second end.

In one embodiment of the invention, the support means comprises a first and a second loop member. Each of these loop members are generally J-shaped and are diametrically opposed to each other. Furthermore, each has a first end which is operably secured to the lens means.

In another embodiment of the invention, the support means comprises a first and a second loop member. Each of these loop members are generally C-shaped and are diametrically opposed to each other. Each of these C-shaped loop members have a first end thereof which is operably secured to the lens means.

In yet another embodiment of the invention, the support means comprises two or more elliptically shaped loop members. Each of these loop members have both of their ends operably affixed to the peripheral edge of the lens means.

In the preferred embodiment of the invention, the support means comprise loop members which are constructed so as to be resiliently compressible, and which have a pre-insertion maximum transverse width which is substantially equal to that of the lens means. Such a construction enables the apparatus itself to be inserted into the eye through a relatively small arc-shaped incision. Once the intraocular lens apparatus is actually inserted into the eye, these resiliently compressed loop members will expand in a transverse direction. Once this expansion has occurred, the resiliently compressed loop members provide maximum retention and stability of the intraocular lens apparatus within the eye.

In another embodiment of the invention, the support means comprise a plurality of loop members which are operably attached to the peripheral edge of the lens means. Each of these loop members are diametrically opposed and arranged radially symmetrically in relation to each other, so as to ensure that the loop members are substantially co-planar with the peripheral edge of the lens means.

In yet another embodiment of the invention, these support means further comprise a plurality of loop members which emanate angularly upwardly with respect to the posterior side of the lens means.

The lens means preferably comprises an optic lens which has an anterior side which is substantially convex. In addition, the lens means is configured in such a way where the posterior side is also substantially convex so as to comprise a bi-convex lens.

In another embodiment of the invention, the lens means comprises an optic lens in which the anterior side is substantially convex. Furthermore, the posterior side of the optic lens has a substantially flat configuration. Alternatively, the posterior side can be substantially concave.

In one embodiment of the invention, the positioning means comprises one or more elliptically shaped portions which are contiguously positioned along the peripheral edge of the lens means. These elliptically shaped portions may comprise aperture means which are integrally positioned within the one or more elliptically shaped portions. The aperture means enable receptive cooperation with a surgical instrument during manipulation of the intraocular lens apparatus.

In another embodiment of the invention, the positioning means further comprise a plurality of slot means which are operably and distally positioned juxtaposed to the peripheral edge of the lens means. Accordingly, these slot means allow for the receptive cooperation of the intraocular lens apparatus with a surgical instrument during manipulation of the intraocular lens apparatus.

DETAILED DESCRIPTION OF THE DRAWINGS

Figure 1:
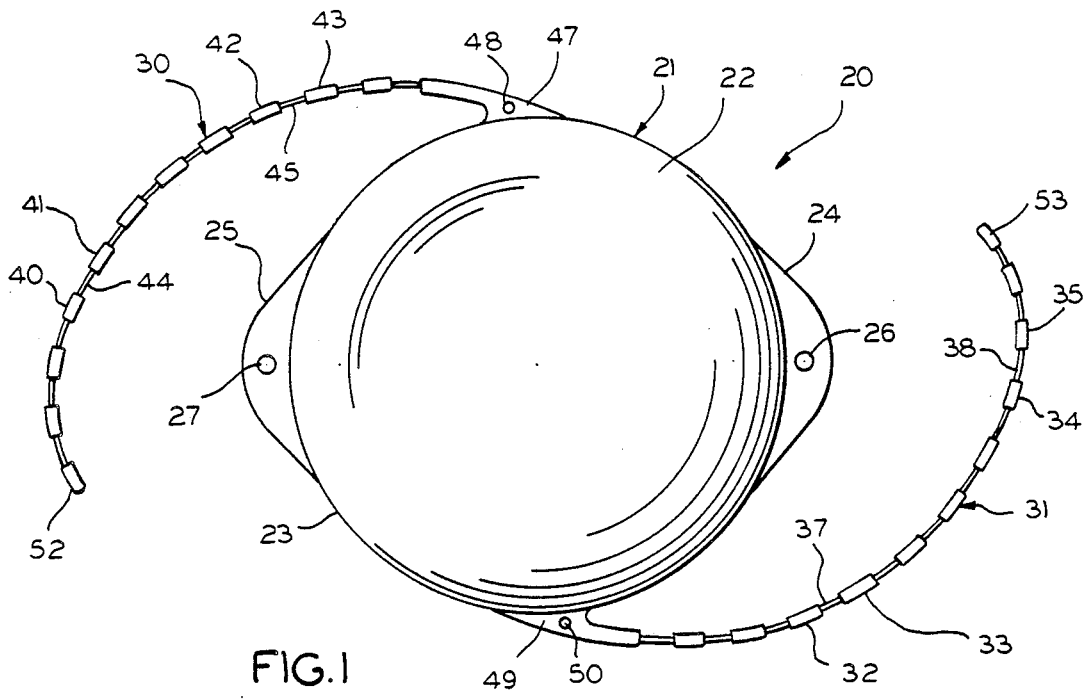
FIG. 1 of the drawings is a top plan view showing, in particular, the inventive posterior chamber IOL apparatus and, the haptics, positioning means and optic lens.

While this invention is susceptible of embodiment in many different forms, there is shown in the drawings and will herein be described in detail, several specific embodiments with the understanding that the present disclosure is to be considered as an exemplification of the principles of the invention and is not intended to limit the invention to the embodiment illustrated.

A first preferred embodiment of posterior chamber intraocular lens apparatus 20 is shown in FIG. 1 as including optic lens 21 and its posterior side 22, as well as haptics 30 and 31 which are used to secure posterior chamber intraocular lens apparatus 20 within the eye. Implantation of an intraocular lens apparatus requires resilient deformation of the free end of the haptic substantially radially inwardly towards the lens. Optic lens 21 is also shown having optional elliptically shaped positioning means 24 and 25 emanating from the peripheral edge 23 of the light-focusing optic lens 21. Lens 21 should be made of a suitable transparent biocompatible material for optical correction such as polymethylmethacrylate (PMMA), silicone, hydrogel or other soft polymers, acrylate or ophthalmic glass, while haptics 30 and 31 may be constructed by biocompatible material such as polypropylene or polymethylmethacrylate. Haptics 30 and 31 are normally rather fine and have an approximately circular cross-section with a diameter of approximately 0.005 inches. The haptics may also be formed of either single or multiple filaments. The positioning means 24 and 25 further include apertures 26 and 27 respectively, which when used in cooperation with a surgical instrument serve to efficiently allow for the manipulating and positioning of the posterior chamber intraocular lens apparatus 20 once inserted within the eye. The positioning means could also comprise apertures (not shown) formed in the outer periphery of the lens 21, as well. Haptics 30 and 31 attach to lens 21 at shoulders 47 and 49 respectively, attached to the peripheral edge 23 of optic lens 21. Haptics 30 and 31 can have optional apertures 48 and 50 respectively, which are formed in shoulders 47 and 49 to further facilitate manipulation of intraocular lens apparatus 20 with a surgical instrument. Haptic 30 is shown having alternating regions of increased, transverse cross-sectional area 40 through 43 and adjacent regions of narrowed cross-sectional area such as 44 and 45, along the length of haptic 30. Haptic 31 is also shown as having alternating regions of increased and reduced transverse cross-sectional area, such as regions of increased cross-sectional areas 32 through 35, and regions of narrowed cross-sectional area 37 and 38. These alternating narrow and wide portions of haptic 30 and 31 serve to allow for greater flexibility, and the maximum length of contact with the interior surface of the eye, which is needed for the aforementioned resilient deformation of the free end of the haptic radially inwardly towards the lens while retaining the requisite rigidity necessary to facilitate proper securement within the eye. Free ends 52 and 53 of haptics 30 and 31, respectively, are also shown in FIG. 1.

Figure 2:
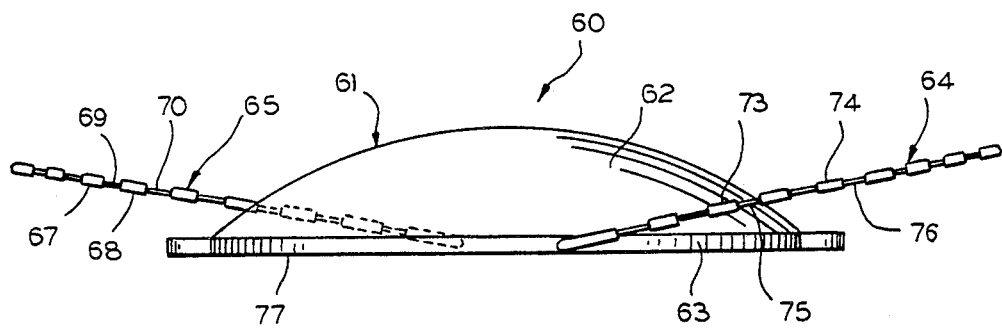
FIG. 2 of the drawings is an elevated side view of one embodiment of the posterior chamber intraocular lens apparatus wherein the haptics are angled upwardly with respect to the posterior side of the optic lens.
Figures 5, 6:
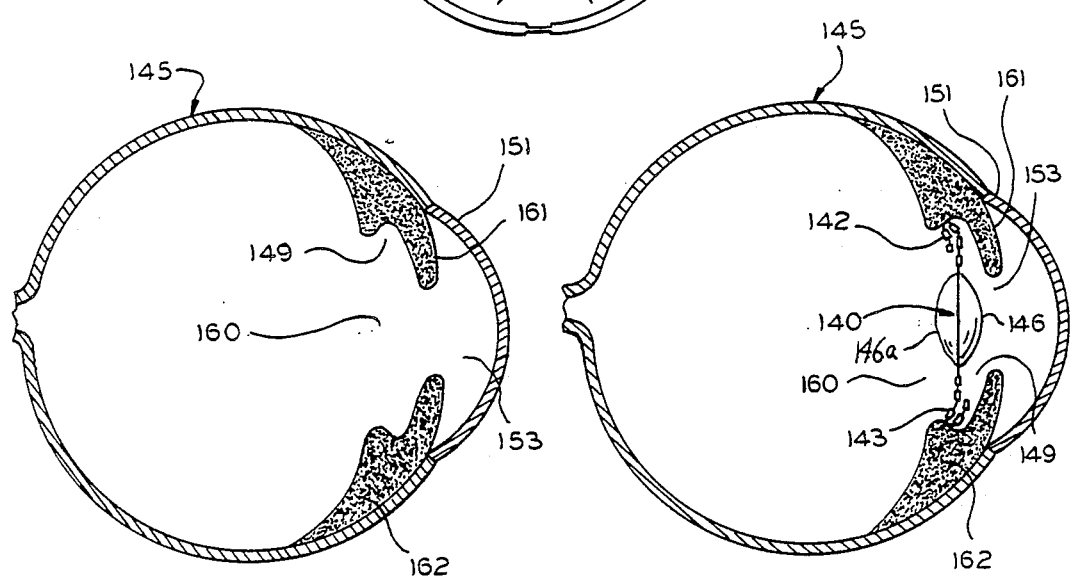
FIG. 5 of the drawings is an elevated cross-sectional side view of a human eye and showing, in particular, the anterior chamber of the eye, the pupilary cavity and the posterior chamber of the eye.
FIG. 6 of the drawings is an elevated side view of the posterior chamber intraocular lens apparatus operably positioned within the posterior chamber of a human eye, and particularly showing the positioning of the optic lens in relation to the pupilary cavity (particularly showing the convex surface of the optic lens)

A preferred embodiment of the invention 60 employing angled haptics 64 and 65 is shown in FIG. 2. These haptics 64 and 65, each have one end affixed to peripheral edge 63 of optic lens 61, and extend upwardly at an angle of approximately 5-20 degrees to the plane of the posterior side 77 of lens 61, and toward anterior side 62 of lens 61 as shown in FIG. 2. Haptics 64 and 65, as shown in FIG. 2, are provided with the above-described alternating regions of increased cross-sectional area such as 67, 68, 73 and 74, and regions of narrowed or decreased cross-sectional area such as 69, 70, 75 and 76. This configuration coupled with the angular positioning of haptics 64 and 65 enable posterior chamber intraocular lens apparatus 60 to be secured within the capsular bag, and in turn, the posterior chamber of the eye 149, as shown in FIG. 6, while allowing each of said haptics to be extremely resiliently compressible.

Figure 3:
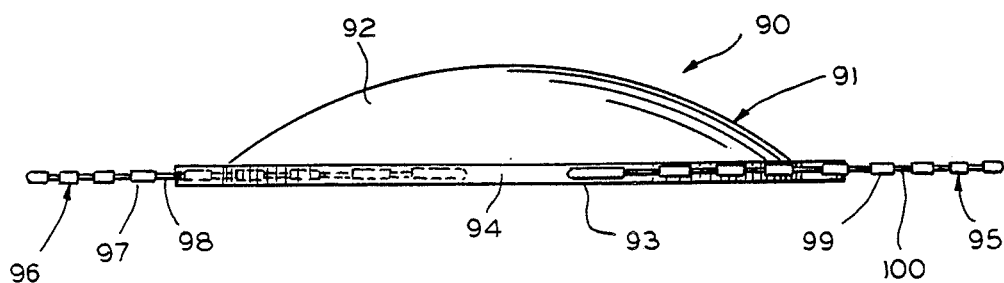
FIG. 3 of the drawings is an elevated side view of another embodiment of the posterior chamber intraocular lens apparatus which shows the haptics being co-planar with the posterior side of the optic lens.

FIG. 3 shows another preferred embodiment of the posterior chamber intraocular lens apparatus 90 as having haptics and 96 being aligned on a plane that is coplanar with the posterior peripheral edge 94 and posterior side 93 of optic lens 91. Anterior side 92 and posterior side 93 of optic lens 91 is also shown in FIG. 3. Haptics 95 and 96 of embodiment 90 of the intraocular apparatus likewise has alternating regions of wide, transverse cross-sectional area, such as 97 and 99 immediately adjacent to narrowed regions such as 98 and 100, respectively.

Figure 4:
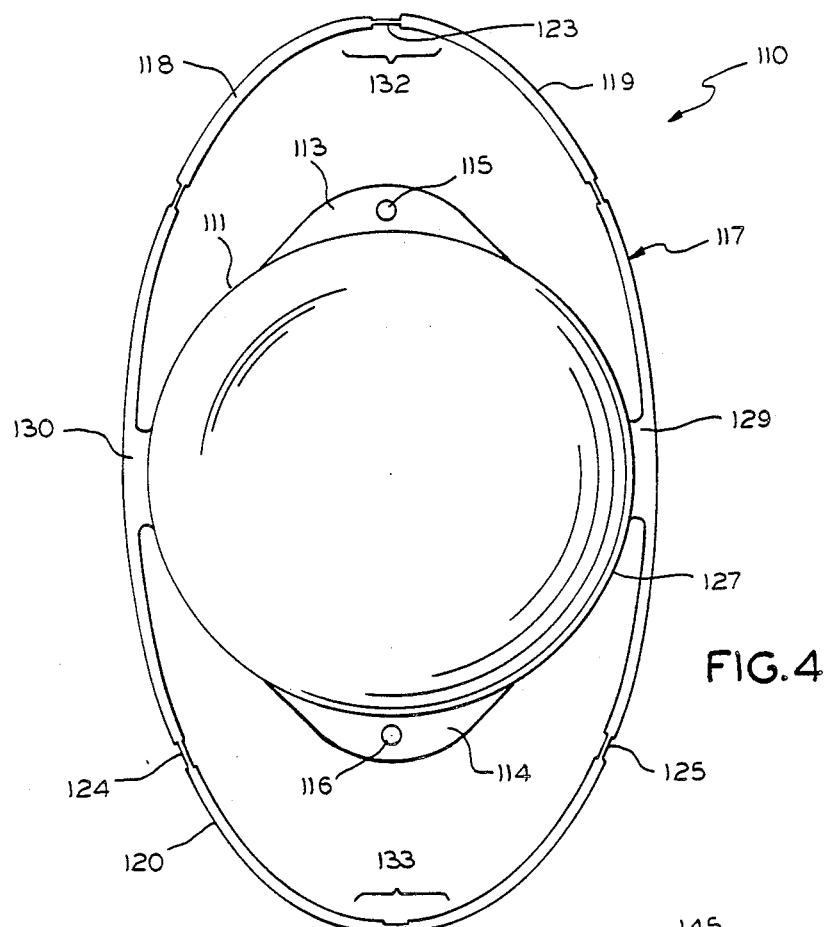
FIG. 4 of the drawings is a top plan view of another embodiment of the posterior chamber intraocular lens apparatus particularly showing the adaptation of a single, oval haptic which is attached at diametrically opposed sides of the optic lens and concentrically positioned about the optic lens itself.

In FIG. 4, another preferred embodiment of posterior chamber intraocular lens apparatus 110 is shown as having a single oval haptic 117 positioned around peripheral edge 127 of optic lens 111. Haptic 117 is attached to optic lens 111 by shoulders 129 and 130 serving as attachment means, which are affixed to peripheral edge 127 of optic lens 111. This single haptic configuration allows intraocular lens apparatus 110 to be inserted within the eye 145, as shown in FIGS. 5 and 6, as a single unit without the need to separately manipulate the haptics. Intraocular lens apparatus 110 is relatively easy to insert, and may further reduce the risk of scratching, and potentially damaging any part of the eye, during such insertion or the subsequent positioning of the lens within the eye.

Single haptic 117 is also configured with a series of wider regions, such as wider regions 118 through 120, and narrower regions, such as 123 through 125, which are positioned adjacent to said wider regions. Accordingly, this alternating sequence of wider regions 118 through 120, and narrower regions 123 through 125, enable maximum flexibility of posterior chamber intraocular lens apparatus 110 prior to and during insertion into the eye, and further allows for maximum spreading of end regions 132 and 133 of haptic 117 along the inside surface of the eye once intraocular lens apparatus 110 is operably positioned therewithin. Varying numbers of narrower and wider regions should also be considered as being contemplated by the present invention.

Also shown in FIG. 4 are elliptically shaped portions 113 and 114 comprising positioning means and their respective apertures 115 and 116, which allow for maneuvering intraocular lens apparatus 110 with surgical instruments to properly align it, once it is actually inserted within the capsular bag of the posterior chamber 149 of the eye 155, as shown in FIGS. 5 and 6. In the preferred embodiment of intraocular lens apparatus 110, narrowed regions such as 123 and 125 of haptic 117 are symmetrically arranged along its length. Moreover, in a preferred embodiment, both wider regions such as 118, 119 and 120 and narrowed regions such as 123 and 125 are each of a substantially constant diameter and substantially circular cross-section, so as to result in substantially uniform stresses being distributed throughout haptic 117, and in turn distributed in a substantially uniform fashion to the interior of the eye once implanted.

In FIGS. 5 and 6, a human eye 145 is shown prior to, and after posterior chamber intraocular lens apparatus 140 has been inserted into the eye 145. In particular, there is shown in FIG. 5, a human eye 145 wherein the natural lens has been extracted because of a cataract condition. Typically, a small incision is made in the front wall of the scleral-corneal junction or interior capsule through the cornea 151. A process such as phacoemulsification is then used to liquify the natural nucleus of the lens prior to removal by suction, or the nucleus can be expressed through a slightly larger incision. The length of the insertion incision should be minimized so as to speed the healing process. Left behind are posterior capsule 160, iris 161 and ciliary sulcus 162. The pupil 153 is ordinarily dilated to facilitate centered positioning of the lens 140 in the posterior chamber 149, behind it.

In order to insert posterior chamber intraocular lens apparatus 140 into eye 145, a small arc-shaped incision (not shown) needs to be made upon the outer periphery of cornea 151. After the incision is made, posterior chamber intraocular lens apparatus 140 is maneuvered and inserted through pupilary cavity 153 until it has entered into posterior chamber 149 of eye 145. Once inserted into posterior chamber 149, posterior chamber intraocular lens apparatus 140 is maneuvered, as shown in FIG. 6, until its convex surface 146 is centered behind pupilary cavity 153, through the use of surgical instruments (not shown). Posterior side 146a is also a substantially convex surface so as to comprise a bi-convex lens together with anterior convex side 146. As shown in FIG. 6, once implanted in the eye, haptics 142 and 143 resiliently expand to contact ciliary sulcus 162 or the capsular bag, so as to assume the shape of the intraocular confines in order to maintain lens apparatus 140 within the interior of the eye 145. Once this has occurred, posterior chamber intraocular lens apparatus 140 will have been appropriately seated and the surgical instruments withdrawn from the interior of the eye 145.

Figure 7:
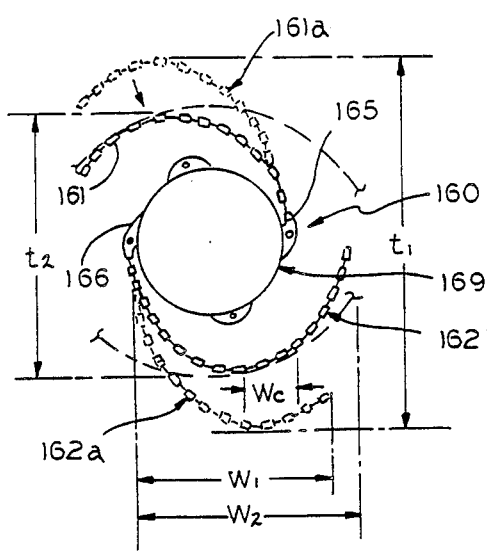
FIG. 7 of the drawings is a top plan view of one embodiment of the posterior chamber intraocular lens apparatus particularly showing the expanded position of the haptics in phantom prior to manipulation and implantation into the eye, and then showing the same haptics after insertion and manipulation with a surgical instrument, through a small axial incision in the eye.

FIG. 7 shows intraocular lens apparatus 160 in the compressed position, as in the interior of the eye, as well as in its expanded position, prior to insertion, in phantom. Haptics 161 and 162 are attached to lens 169 at shoulders 165 and 166. The maximum, pre-insertion longitudinal length dimension is shown as $t_1$. As further shown in FIG. 7, the maximum transverse width dimension of lens apparatus 160 is kept to a minimum to provide the narrowest possible transverse profile for insertion purposes. However, upon implantation, the longitudinal length dimension $t_2$ is shorter than original length dimension $T_1$, due to the compression of haptics 161a and 162a along the longitudinal axis to arrive at post-insertion haptic positions 161 and 162. At the same time, upon insertion of lens apparatus 160, the maximum transverse width dimension increases from $W_1$, to $W_2$, due to the resilient spreading of haptics 161a and 162a in the transverse direction. The alternating regions of wider and narrower haptic cross-section enable the maximum amount of such spreading of the haptics in the transverse direction so as to maximize the region of contact $W_c$ of haptics 161 and 162 with the interior of the eye, while still providing a transverse profile substantially equal to the width of the lens portion. This combines to enable ease of implantation through the smallest possible incision and greater stability once implanted, through maximized region of contact $W_c$ along the interior of the eye.

Figure 8:
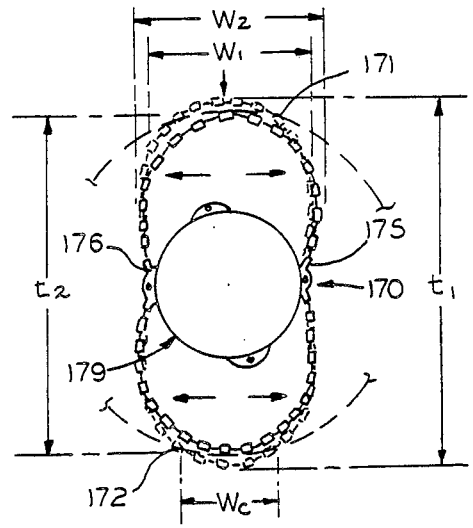
FIG. 8 of the drawings is a top plan view of another embodiment of the posterior chamber intraocular lens apparatus and showing, in particular, the oval, single haptic attached to the outer periphery of the optic lens at diametrically opposed points thereon, with the expanded position, prior to insertion being shown in phantom and the compressed position once manipulated and implanted in the eye through a small incision in solid.

Another embodiment of intraocular lens apparatus 170 is shown in FIG. 8. In this embodiment, both ends of haptics 171 and 172 remain attached to lens 179 at shoulders 175 and 176. The pre-insertion configuration is shown in phantom. Once implanted in the interior of the eye, longitudinal length dimension of apparatus 170 decreases from $T_1$ to $T_2$, while transverse width dimension increases from $W_1$ to $W_2$. The region of contact $W_c$ of the haptics with the interior of the eye is likewise maximized with the present embodiment of the invention.

Figure 9:
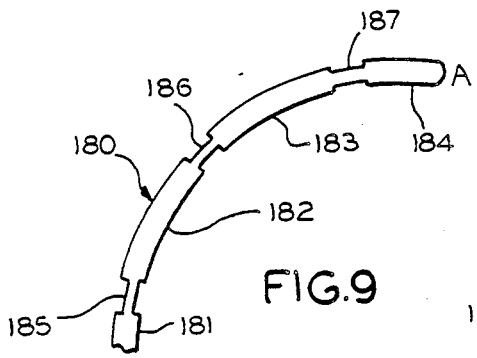
FIG. 9 of the drawings is a top cutaway view of one embodiment of the present invention having a haptic construction with a number of regions of narrowed cross-sectional area wherein the transverse cross-sectional area of each such region successively increases from that of the next preceding region as one moves in the direction of the free end of the haptic.

In FIG. 9, one embodiment of haptic 180 is shown having wide portions 181 through 184, and narrow portions 185 through 187. Each narrow portion, such as 185 through 187, has a constant and progressively larger transverse cross-sectional area than the preceding narrow portion preceding it, as one moves toward the free end A of haptic 180. Accordingly, haptic 180 will be less flexible near its free end A, than at its point of attachment to the lens, so as to spread less against the interior of the eye near the free end A than near the attached end of the haptic.

Figure 10:
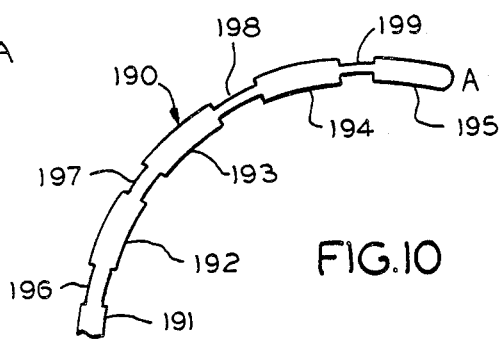
FIG. 10 of the drawings is a top cutaway view of another embodiment of the invention having a haptic construction wherein the transverse cross-sectional area of each narrowed region successively decreases in the direction of the free end of the haptic.

In FIG. 10, another embodiment of haptic 190 is shown having regions of wider cross-sectional area 191 through 195 and regions of narrowed cross-sectional area 196 through 199 which are adjacently positioned thereto. In this particular embodiment, each individual region of narrowed constant cross-sectional sectional area, such as narrowed regions 196 through 199, have a smaller transverse cross-sectional area than each respective preceding region of narrowed cross-sectional area, as one moves toward the free end A of haptic 190. This configuration allows for greater rigidity and therefore lens flexibility closer the attached end of the haptic and greater deflection and flexibility near the free end A of haptic 190.

Figure 11:
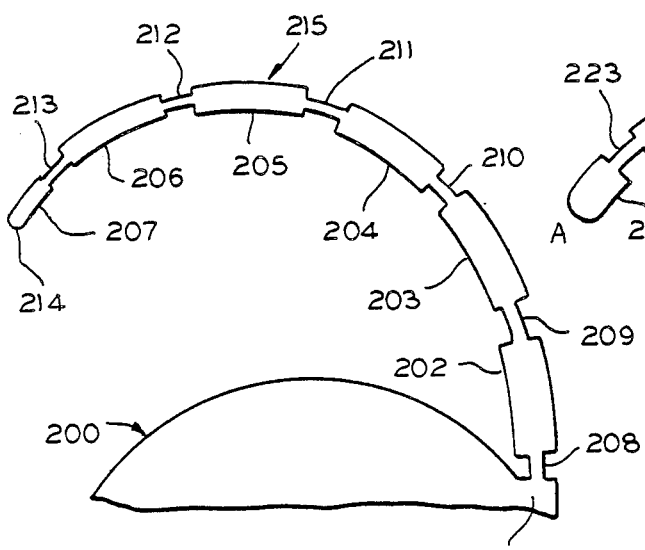
FIG. 11 of the drawings is a top cutaway view of another embodiment of the posterior chamber intraocular lens apparatus having a haptic construction with a number of regions of increased cross-sectional area wherein the transverse cross-sectional area of each such increased region successively decreases in the direction of the free end of the haptic.

Another embodiment of haptic 215 is shown in FIG. 11 wherein regions of enlarged transverse cross-sectional area 202 through 207 each have constant transverse cross-sectional areas that are smaller than the next preceding regions of enlarged cross-sectional area. The transverse cross-sectional areas of enlarged regions 202 through 207, each decrease as one moves to free end 214 of haptic 215 and away from attachment 201 on lens 200. In this embodiment, regions of narrowed transverse cross-sectional area 208 through 213 have substantially uniform transverse cross-sectional areas throughout the entire length of haptic 215, however, in other embodiments, these narrowed regions 208 through 213 can also decrease or increase in cross-sectional area as one moves toward free end 214 of haptic 215. This particular configuration allows for greater rigidity closest to securement point 201 of haptic 215 while allowing greater flexibility near tip 214 of haptic 215.

Figure 12:
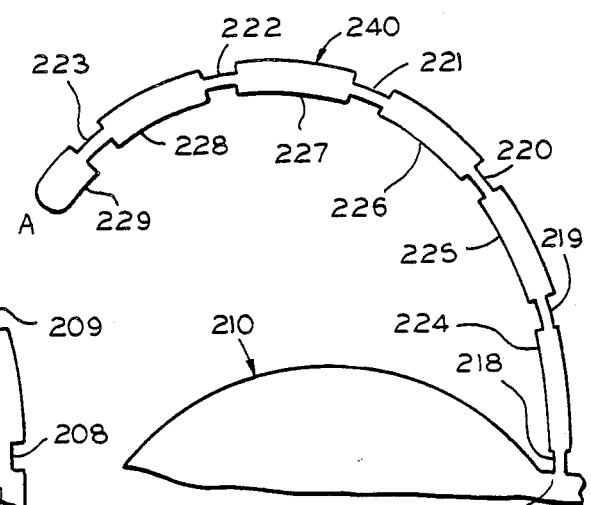
FIG. 12 of the drawings is top cutaway view of another embodiment of the posterior chamber intraocular lens apparatus having a haptic construction wherein the transverse cross-sectional area of each increased region successively increases in the direction of the free end of the haptic.

In FIG. 12, another embodiment of haptic 240 is shown having regions of enlarged transverse cross-sectional area 224 through 229 interposed between regions of narrow portions 218 through 223. In this embodiment, while each narrowed transverse cross-sectional area 218 through 223 has a substantially uniform transverse cross-sectional area, regions of enlarged cross section 224 through 229 each have increasingly larger transverse cross-sectional areas than the next preceding enlarged region as one moves towards free end A of haptic 290. This particular configuration allows greater flexibility near securement point 231 of optic lens 210, while providing for greater rigidity and stability at the free end of haptic 240.

The foregoing description and drawings merely explain and illustrate the invention and the invention is not limited thereto except insofar as the appended claims are so limited as those skilled in the art who have the disclosure before them will be able to make modifications and variations therein without departing from the scope of the invention.

What is claimed is:

1. An intraocular lens apparatus for implantation in the posterior chamber of an eye, in which said apparatus is inserted into an eye along a longitudinal direction through an incision made in the eye, said apparatus having strong, yet flexible support means for positioning and maintaining of said position of said apparatus within the interior of the eye, and further enabling ease in manipulation, rotation and positioning of said apparatus after insertion into said posterior chamber of the eye, said intraocular lens apparatus comprising:

substantially circular lens means having an anterior side, an opposite posterior side and a peripheral edge;

positioning means operably attached to said lens means for enabling facilitated manipulation of said intraocular lens apparatus once the apparatus is inserted within the eye for proper positioning therein;

resilient support means operably attached to said lens means and extending outwardly therefrom, for retaining and stabilizing said intraocular lens apparatus once appropriately located within the eye by contacting said eye interior along a region of contact, and said support means comprising at least one flexible loop member having a plurality of regions of increased cross-section, each positioned adjacent to a region of narrowed cross-section along its length, so as to comprise alternating regions of increased and decreased cross-section with at least, one of said regions of increased cross-section having a substantially continuous transverse cross-section along its length, for increasing flexibility of said at least one loop member and provide a maximized region of contact within said interior of said eye, while simultaneously enabling said intraocular lens apparatus to be inserted into the eye through a relatively small axial incision.

2. The invention according to claim 1 wherein said support means further comprises:

said loop member being operably attached at a first end to said peripheral edge of said lens means and ending at a second end;

said regions of narrowed cross-section of said loop member having successively smaller transverse cross sectional areas than the next preceding region of narrowed cross-section; and each of said regions of said narrowed cross-sections decreasing in transverse cross-sectional area along the length of said loop member from said first end to said second end, so as to provide for greater flexibility of said loop member proximate to said second end thereof.

3. The invention according to claim 1 wherein said support means further comprises:

said loop member being operably attached at a first end to said peripheral edge of said lens means and ending at a second end;

each of said regions of narrowed cross-section of said loop member having successively smaller transverse cross sectional areas than the next preceding region of said narrowed cross-section; and each of said regions of narrowed cross-sections increasing in transverse cross-sectional area along the length of said loop member from said first end to said second end, so as to provide for greater flexibility of said loop member proximate to said first end.

4. The invention according to claim 1 wherein said support means further comprises:

said loop member being operably attached at a first end to said peripheral edge of said lens means and ending at a second end;

each of said regions of increased cross-section of said loop member having successively smaller transverse cross sectional areas than the next preceding region of increased cross-section; and each of said regions of increased cross-sections increasing in transverse cross-sectional area along the length of said loop member from said first end to said second end, so as to provide for greater flexibility of said loop member proximate to said first end.

5. The invention according to claim 1 wherein said support means further comprises:

said loop member being operably attached at a first end to said peripheral edge of said lens means and ending at a second end;

each of said regions of increased cross-section of said loop member having successively smaller transverse cross-sectional areas than the next preceding regions of increased cross-section; and each of said regions of increased cross-section decreasing in transverse cross-sectional area along the length of said loop member from said first end to said second end, so as to provide for greater flexibility of said loop member proximate to said second end.

6. The invention according to claim 1 wherein said support means comprises first and second generally J-shaped generally diametrically opposed loop members, each having a first end thereof operably secured to said lens means.

7. The invention according to claim 1 wherein said support means comprises first and second generally C-shaped generally diametrically opposed loop members, each having a first end thereof operably secured to said lens means.

8. The invention according to claim 1 wherein said support means comprises one substantially oval shaped loop operably attached and positioned around the periphery of said lens means.

9. The invention according to claim 1 wherein said support means comprises:

said loop members being constructed to be resiliently compressible and having a pre-insertion maximum transverse width substantially equal to that of said lens means so as to enable said apparatus to be inserted into the eye through a relatively small axial incision; and said resiliently compressed loop members thereby expanding in a transverse direction upon insertion into the eye so as to enable maximum retention and stability of said intraocular lens apparatus after said insertion into the eye.

10. The invention according to claim 9 wherein said support means comprises:

a plurality of loop members operably attached to said peripheral edge of said lens means; and said plurality of loop members each being diametrically opposed and radially symmetrical in relation to each other, whereby said plurality of loop members are substantially co-planar with said peripheral edge of said lens means.

11. The invention according to claim 10 wherein said support means further comprises:

said plurality of loop members emanating angularly upwardly with respect to said posterior side of said lens means.

12. The invention according to claim wherein said lens means comprises:

an optic lens, wherein both said anterior side and said posterior side thereof are substantially convex, so as to comprise a substantially bi-convex lens.

13. The invention according to claim 1 wherein said lens means comprises:

an optic lens, wherein said anterior side is substantially convex and said posterior side is substantially flat.

14. The invention according to claim 1 wherein said positioning means comprises:

one or more elliptically shaped portions contiguously positioned along said peripheral edge of said lens means.

15. The invention according to claim 14 wherein said one or more elliptically shaped portions comprises:

aperture means integrally positioned within said one or more elliptically shaped portions for receptive cooperation with a surgical instrument during said manipulation of intraocular lens apparatus.

16. The invention according to claim 14 wherein said positioning means further comprises:

a plurality of aperture means operably and distally positioned juxtaposed to said peripheral edge of said lens means for receptive cooperation with a surgical instrument during said manipulation of said intraocular lens apparatus.

* * * * *

UNITED STATES PATENT AND TRADEMARK OFFICE
CERTIFICATE OF CORRECTION

PATENT NO. : 4,990,159
DATED : February 5, 1991
INVENTOR(S) : Manus C. Kraff

It is certified that error appears in the above-identified patent and that said Letters Patent is hereby corrected as shown below:

Col. 7, Line 17  Delete "haptics" and insert instead --haptics 95--.

Col. 7, Line 61  Delete "eye 155," and insert instead --eye 145,--.

Col. 9, Line 1  Delete "incision" and insert instead --incision,--.

Col. 9, Line 31  Delete "cross-sectional sectional" and insert instead --cross-sectional--.

Col. 12, Line 30  Delete "claim wherein" and insert instead --claim 1 wherein--.

Signed and Sealed this

Fourth Day of August, 1992

Attest:

DOUGLAS B. COMER

*Attesting Officer*  *Acting Commissioner of Patents and Trademarks*